US00PP24480P2

(12) United States Plant Patent
Kaagman

(10) Patent No.: US PP24,480 P2
(45) Date of Patent: May 20, 2014

(54) OSTEOSPERMUM PLANT NAMED 'OSTZ0003'

(50) Latin Name: *Osteospermum ecklonis*
Varietal Denomination: OSTZ0003

(71) Applicant: Syngenta Crop Protection AG, Basel (CH)

(72) Inventor: Pim Kaagman, Bovenkarspel (NL)

(73) Assignee: Syngenta Crop Protection AG, Basel (CH)

( * ) Notice: Subject to any disclaimer, the term of this patent is extended or adjusted under 35 U.S.C. 154(b) by 45 days.

(21) Appl. No.: 13/694,031

(22) Filed: Oct. 22, 2012

(51) Int. Cl.
*A01H 5/00* (2006.01)

(52) U.S. Cl.
USPC ..... Plt./360

(58) Field of Classification Search
CPC ..... A01H 5/025; A01H 5/02; A01H 5/00
USPC ..... Plt./360
See application file for complete search history.

*Primary Examiner* — Kent L Bell
(74) *Attorney, Agent, or Firm* — Joshua L. Price

(57) ABSTRACT

A new *Osteospermum* plant named 'OSTZ0003' particularly distinguished by the yellow colored inflorescences held nicely above the foliage, medium-green foliage, with early flowering and an excellent branched and compact bushy habit.

1 Drawing Sheet

Latin name of the genus and species of the plant claimed: *Osteospermum ecklonis*.

Varietal denomination: 'OSTZ0003'.

BACKGROUND OF THE NEW PLANT

The present invention comprises a new *Osteospermum*, botanically known as *Osteospermum ecklonis*, and hereinafter referred to by the variety name 'OSTZ0003'.

'OSTZ0003' is a product of a planned breeding program. The new cultivar 'OSTZ0003' has yellow colored inflorescences held nicely above the foliage, medium-green foliage, with early flowering and an excellent branched and compact bushy habit.

'OSTZ0003' originates from an open-pollinated hybridization made in August 2007 in greenhouse in Andijk, The Netherlands. The female parent was an unpatented, proprietary plant identified as '98-10' with bronze-yellow color, with a later flowering habit and fewer branches when compared to 'OSTZ0003'.

The male parent of 'OSTZ0003' is unknown. The resultant seed was sown in March 2008. 'OSTZ0003' was selected as one flowering plant within the progeny of the stated cross in August 2008 in a greenhouse in Andijk, The Netherlands.

The first act of asexual reproduction of 'OSTZ0003' was accomplished when vegetative cuttings were propagated from the initial selection in August 2008 in a greenhouse in Andijk, The Netherlands.

BRIEF SUMMARY OF INVENTION

Horticultural examination of plants grown from cuttings of the plant initiated in August, 2008 in Andijk, The Netherlands, and continuing thereafter, has demonstrated that the combination of characteristics as herein disclosed for 'OSTZ0003' are firmly fixed and are retained through successive generations of asexual reproduction.

Plant Breeder's Rights for this cultivar were applied for in Canada on Nov. 1, 2011 (11-7413) and at the Community Plant Variety Office on Jul. 20, 2012 (2012/1620). 'OSTZ0003' has not been made publicly available more than one year prior to the filing of this application.

'OSTZ0003' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Osteospermum* as a new and distinct variety.

BRIEF DESCRIPTION OF THE PHOTOGRAPHS

The accompanying photographic drawing shows typical flower and foliage characteristics of 'OSTZ0003' with colors being as true as possible with an illustration of this type. The photographic drawing shows in FIG. 1 a flowering plant of the new variety and in FIG. 2 a close-up of an inflorescence.

DETAILED BOTANICAL DESCRIPTION

The plant measurements and descriptions were taken in Enkhuizen, The Netherlands, in early September 2012 using plants that were growing in a field trial and were about 27 weeks of age.

Figure 1:
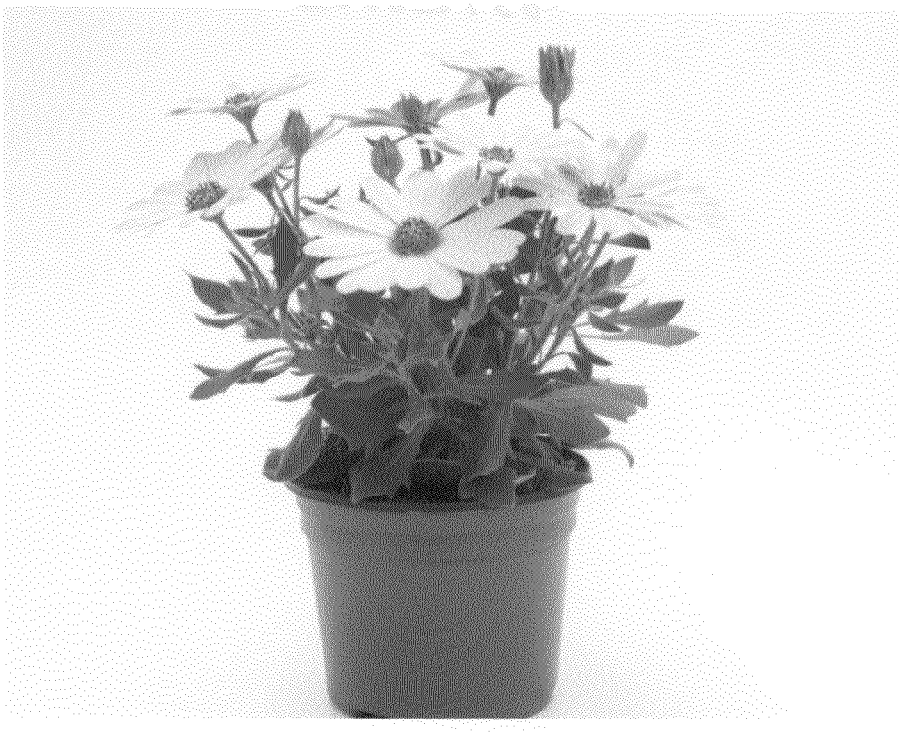
Figure 2:
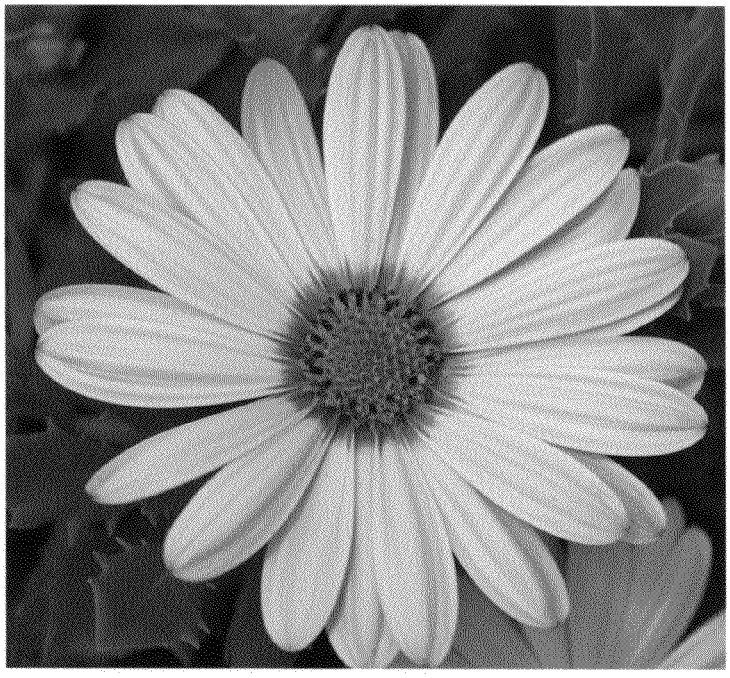

The aforementioned photograph for FIG. 1 was taken in Enkhuizen, The Netherlands in April 2011. The plants were growing in 10 cm pots in a greenhouse trial and were about 13 weeks of age. The aforementioned photograph for FIG. 2 was taken in Gilroy, Calif. in April 2011. The plants used were growing in 4.5 inch pots in a greenhouse trial and were about 13-14 weeks of age.

Color references are made to The Royal Horticultural Society Colour Chart (R.H.S.) 2001.

TABLE 1

DIFFERENCES BETWEEN THE NEW VARIETY 'OSTZ0003' AND A SIMILAR VARIETY

| | 'OSTZ0003' | 'Tra Yel' (U.S. Plant Pat. No. 20,178) |
|---|---|---|
| Branching habit: | More branches | Fewer branches |
| Flowering response: | Earlier | Later |
| Inflorescence size: | Smaller | Larger |

Plant:

*Form, growth and habit*.—Compact and bushy growth habit with a moderately tight canopy of branches, with the inflorescences held well above the foliage.

*Plant height*.—About 23.0 cm.

*Plant height* (*inflorescence included*).—About 33.0 cm.

*Plant width*.—About 44.0 cm.

Roots:

*Number of days to initiate and develop roots*.—24-27 days at about 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 146B.

*Immature, leaf color, lower surface*.—RHS 146C.

*Mature, leaf color, upper surface*.—RHS 146A.

*Mature, leaf color, lower surface*.—RHS 146B.

*Length*.—3.5-6.0 cm.

*Width*.—1.5-2.5 cm.

*Shape*.—Spathulate.

*Base shape*.—Attenuate.

*Apex shape*.—Obtuse.

*Margin*.—Dentate.

*Texture, upper surface*.—Slightly rough but otherwise glabrous.

*Textures, lower surface*.—Hirsutullous.

*Color of veins, upper surface*.—RHS 144B.

*Color of veins, lower surface*.—RHS 144A.

*Pattern of veining*.—Pinnate.

*Petiole color*.—RHS 144B.

*Length*.—1-1.5 cm.

*Diameter*.—0.2 cm.

*Texture*.—Glabrous.

Stem:

*Quantity of main branches per plant*.—About 5.

*Color of stem*.—RHS 14B to RHS 144C covered with anthocyanins of a light hue of RHS 183D.

*Length of stem*.—18-20.0 cm.

*Diameter*.—0.4-0.6 cm.

*Length of internodes*.—0.5-1.5 cm.

*Texture*.—Glabrous.

*Color of peduncle*.—RHS 144B to RHS 144C covered with anthocyanins of RHS N186D.

*Length of peduncle*.—6-12.0 cm.

*Peduncle diameter*.—0.3 cm.

*Texture*.—Glabrous.

Inflorescence:

*Type*.—Compositate type, solitary inflorescences borne terminally above foliage, with 2 whorls of ray florets.

*Quantity of inflorescences per plant*.—About 40 with about 30 buds.

*Lastingness of individual blooms on the plant*.—About 1 week depending on temperature.

*Fragrance*.—None.

Bud (just when opening/showing color):

*Color*.—RHS 9B with a longitudinal stripe about RHS166A down the middle.

*Length*.—1.0 cm.

*Width*.—1-1.5 cm.

*Shape*.—Oblate.

Immature inflorescence:

*Diameter*.—3.5 cm.

*Color of ray florets upper surface*.—RHS 9A to RHS 9C at the base.

*Lower surface*.—RHS 9A to RHS 9C with a broad longitudinal stripe of RHS 200D down the middle.

*Length*.—1.8-2.1 cm.

*Width*.—0.5 cm.

Mature inflorescence:

*Diameter*.—4.5-5.5 cm.

*Depth*.—1-1.3 cm.

*Total diameter of disc*.—1.0 cm.

*Receptacle color*.—RHS 144C.

*Receptacle height*.—0.25 cm.

*Receptacle diameter*.—0.4 cm.

Ray florets:

*Quantity of florets*.—13-17.

*Color of florets, upper surface*.—RHS 9A to RHS 9C with small blotch of RHS 186D basally.

*Color of florets, lower surface*.—RHS 9A with slight blotches of about RHS 200D and RHS 187B longitudinally down the center.

*Length*.—2.4-2.6 cm.

*Width*.—0.6 cm.

*Shape*.—Elliptical.

*Apex shape*.—Obtuse.

*Margin*.—Entire.

*Texture, upper surface*.—Papillose.

*Texture, lower surface*.—Papillose.

Disc florets:

*Average quantity of florets*.—About 76.

*Color of florets*.—RHS 155B with RHS 1D basally and RHS 199C at the apex.

*Length*.—0.6-0.7 cm.

*Width*.—0.1-0.15 cm.

*Shape*.—Tubular, elongated.

*Apex shape*.—Acute, 5 pointed.

Phyllaries:

*Quantity*.—15-20.

*Color, outer surface*.—RHS 146A.

*Color, inner surface*.—RHS 146B.

*Length*.—1.1 cm.

*Width*.—0.1 cm.

*Shape*.—Lanceolate.

*Apex shape*.—Acute.

*Base*.—Fused.

*Margins*.—Entire.

*Texture, outer surface*.—Pubescent.

*Texture, inner surface*.—Glabrous.

Reproductive organs:

*Gynoceium*.—Pistil: 1. Length: 0.4 cm. Style color: RHS 16D. Style length: 0.2 cm. Stigma color: RHS 9C with RHS 200A margins. Stigma shape: Bi-parted. Ovary color: RHS 144B. Ovary length: 0.3 cm. Ovary diameter: 0.15 cm.

*Androecium*.—Stamens: 1. Color of filaments: RHS 155D. Length filaments: 0.4 cm. Anther color: RHS 200D. Anther length: 0.1 cm. Color of pollen: RHS 17C. Pollen amount: Normal.

*Fertility/seed set*.—Has not been determined to date.

*Disease/pest resistance*.—Has not been determined to date.

What is claimed is:

1. A new and distinct variety of *Osteospermum* plant named 'OSTZ0003' substantially as illustrated and described herein.

* * * * *